United States Patent
Lebel et al.

(10) Patent No.: US 6,915,147 B2
(45) Date of Patent: Jul. 5, 2005

(54) SENSING APPARATUS AND PROCESS

(75) Inventors: Ronald J. Lebel, Sherman Oaks, CA (US); Rajiv Shah, Rancho Palo Verde, CA (US); Yanan Zhang, Valencia, CA (US); Edward Chernoff, Frazier Park, CA (US); Rudolph A. Montalvo, Woodland Hills, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 302 days.

(21) Appl. No.: 10/036,093

(22) Filed: Dec. 28, 2001

(65) Prior Publication Data

US 2003/0050547 A1 Mar. 13, 2003

Related U.S. Application Data

(60) Provisional application No. 60/318,060, filed on Sep. 7, 2001.

(51) Int. Cl.[7] ................................................. A61B 5/00
(52) U.S. Cl. ....................... 600/322; 600/345; 600/347; 600/365; 600/485; 600/500; 600/504; 600/540; 600/561
(58) Field of Search ................................. 600/345–365, 600/504–5, 327, 332, 339, 485, 549, 561, 505, 486, 488, 322–325

(56) References Cited

U.S. PATENT DOCUMENTS

| | | | |
|---|---|---|---|
| 4,240,438 A | 12/1980 | Updike et al. | |
| 4,479,796 A | 10/1984 | Kallok | |
| 4,484,987 A | 11/1984 | Gough | |
| 4,568,335 A | 2/1986 | Updike et al. | |
| 4,628,928 A | 12/1986 | Lowell | |
| 4,650,547 A | 3/1987 | Gough | |
| 4,703,756 A | 11/1987 | Gough et al. | |
| 4,757,022 A | 7/1988 | Shults et al. | |
| 4,771,772 A | 9/1988 | DeWitt | |
| 4,865,038 A * | 9/1989 | Rich et al. | 600/344 |
| 4,867,557 A * | 9/1989 | Takatani et al. | 356/41 |
| 4,890,620 A | 1/1990 | Gough | |
| 4,911,168 A | 3/1990 | Davis | |
| 4,957,110 A * | 9/1990 | Vogel et al. | 600/381 |
| 4,994,167 A | 2/1991 | Shults et al. | |
| 5,094,951 A | 3/1992 | Rosenberg | |
| 5,266,688 A | 11/1993 | Rosenberg | |
| 5,328,460 A | 7/1994 | Lord et al. | |
| 5,497,772 A | 3/1996 | Schulman et al. | |
| 5,534,025 A | 7/1996 | Moussy | |
| 5,593,852 A | 1/1997 | Heller et al. | |
| 5,660,163 A | 8/1997 | Schulman et al. | |
| 5,667,983 A | 9/1997 | Abel et al. | |
| 5,696,314 A | 12/1997 | McCaffrey et al. | |
| 5,707,502 A | 1/1998 | McCaffrey et al. | |

(Continued)

FOREIGN PATENT DOCUMENTS

WO     WO 01/01851 A1     11/2001

OTHER PUBLICATIONS

PCT International Search Report as issued in International Application No. PCT/US02/28017, Mailing date May 3, 2003.

*Primary Examiner*—Robert L. Nasser
(74) *Attorney, Agent, or Firm*—Foley & Lardner LLP

(57) ABSTRACT

A sensing apparatus with a connector, a sensor lead and a sensor module with a spacer placed over electrodes that have been deposited on a substrate. The spacer may have a space for receiving an enzyme. End portions of the sensor module may be encapsulated, such as with molded beads. A sensor lead may attach to the sensor module and may have an outer tubing that passes over the module and attaches to the beads at the end of the sensor module. The sensor lead may also attach to the connector such that the sensing apparatus may be electrically coupled to a pump, electronics or other devices. The sensing apparatus may be implanted into a vein or artery.

10 Claims, 9 Drawing Sheets

U.S. PATENT DOCUMENTS

| | | | |
|---|---|---|---|
| 5,711,868 A | 1/1998 | Maley et al. | |
| 5,728,281 A | 3/1998 | Holmstrom et al. | |
| 5,741,211 A | 4/1998 | Renirie et al. | |
| 5,741,319 A | 4/1998 | Woloszko et al. | |
| 5,770,028 A | 6/1998 | Maley et al. | |
| 5,773,270 A | 6/1998 | D'Orazio et al. | |
| 5,791,344 A | 8/1998 | Schulman et al. | |
| 5,804,048 A | 9/1998 | Wong et al. | |
| 5,919,216 A | 7/1999 | Houben et al. | |
| 5,932,175 A | 8/1999 | Knute et al. | |
| 5,941,906 A | 8/1999 | Barreras, Sr. et al. | |
| 5,965,380 A | 10/1999 | Heller et al. | |
| 5,985,129 A | 11/1999 | Gough et al. | |
| 5,992,211 A | 11/1999 | Skrtic | |
| 6,001,067 A | 12/1999 | Shults et al. | |
| 6,002,954 A | 12/1999 | Van Antwerp et al. | |
| 6,027,479 A | 2/2000 | Alei et al. | |
| 6,049,727 A | 4/2000 | Crothall | |
| D424,696 S | 5/2000 | Ray et al. | |
| D426,638 S | 6/2000 | Ray et al. | |
| 6,093,167 A | 7/2000 | Houben et al. | |
| 6,103,033 A | 8/2000 | Say et al. | |
| 6,120,676 A | 9/2000 | Heller et al. | |
| 6,122,536 A | 9/2000 | Sun et al. | |
| 6,125,290 A | 9/2000 | Miesel | |
| 6,125,291 A | 9/2000 | Miesel et al. | |
| 6,134,459 A | 10/2000 | Roberts et al. | |
| 6,135,978 A | 10/2000 | Houben et al. | |
| 6,143,150 A * | 11/2000 | Nagai et al. | 600/353 |
| 6,144,866 A | 11/2000 | Miesel et al. | |
| 6,159,240 A | 12/2000 | Sparer et al. | |
| 6,162,611 A | 12/2000 | Heller et al. | |
| 6,163,723 A | 12/2000 | Roberts et al. | |
| 6,175,752 B1 | 1/2001 | Say et al. | |
| 6,198,952 B1 | 3/2001 | Miesel | |
| 6,201,980 B1 | 3/2001 | Darrow et al. | |
| 6,248,067 B1 | 6/2001 | Causey, III et al. | |
| 6,248,080 B1 | 6/2001 | Miesel et al. | |
| 6,251,260 B1 | 6/2001 | Heller et al. | |
| 6,256,525 B1 * | 7/2001 | Yang et al. | 600/373 |
| 6,259,937 B1 | 7/2001 | Schulman et al. | |
| 6,261,280 B1 | 7/2001 | Houben et al. | |
| 6,268,161 B1 | 7/2001 | Han et al. | |
| 6,295,476 B1 * | 9/2001 | Schaenzer | 607/122 |
| 6,317,615 B1 * | 11/2001 | KenKnight et al. | 600/372 |
| 6,411,834 B1 * | 6/2002 | Nagai | 600/348 |
| 6,456,863 B1 * | 9/2002 | Levin et al. | 600/374 |
| 6,466,810 B1 * | 10/2002 | Ward et al. | 600/345 |

* cited by examiner

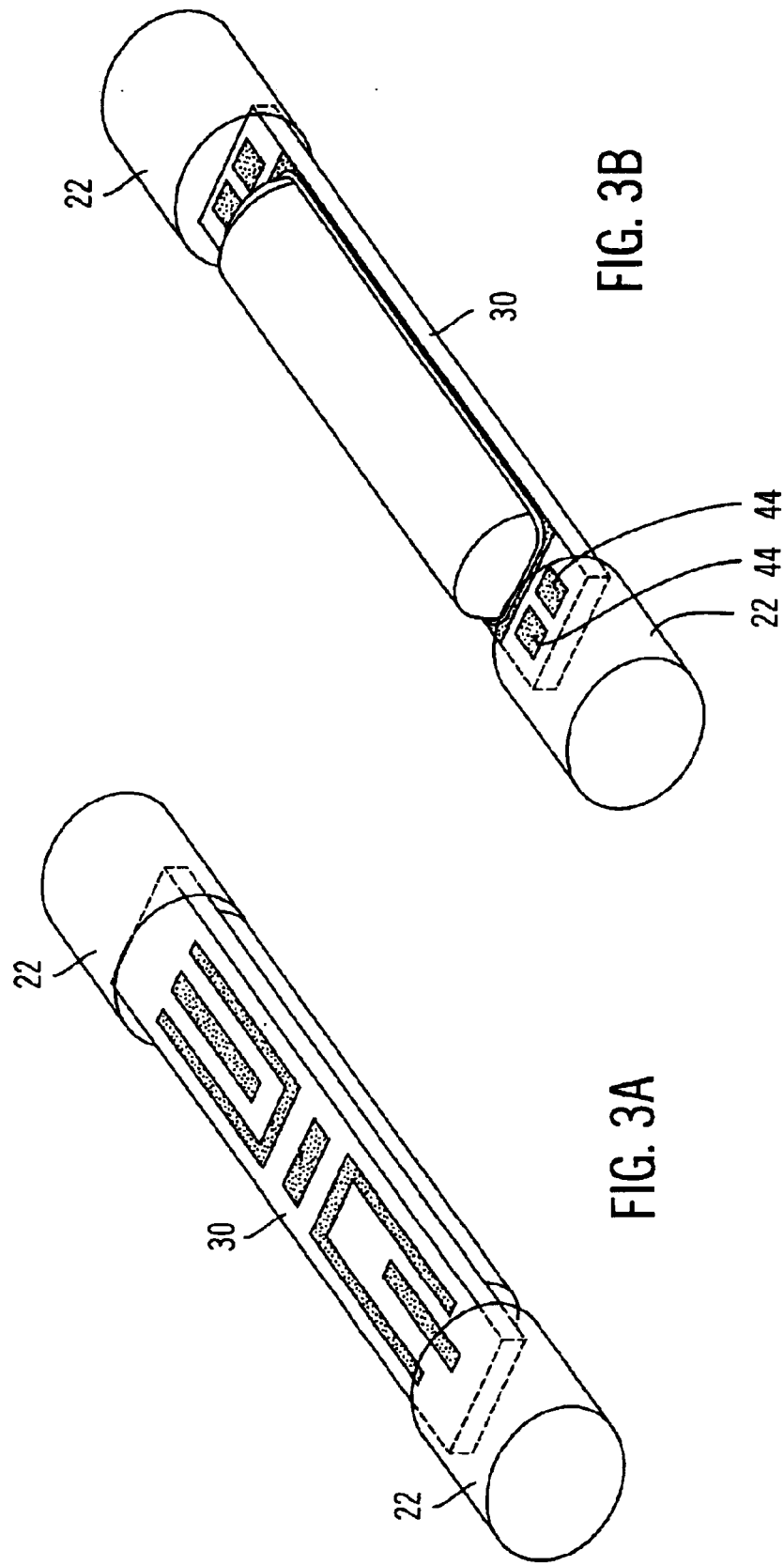

SENSING APPARATUS AND PROCESS

CROSS-REFERENCE TO RELATED APPLICATIONS

Embodiments of the present invention claim priority from a U.S. Provisional Application entitled "Sensing Apparatus and process," Ser. No. 60/318,060 filed Sep. 7, 2001, the contents of which are incorporated by reference herein.

BACKGROUND

1. Field of the Invention

The present invention relates to the field of sensor technology and, in particular, to implantable, in-vivo sensing systems used for sensing a variety of parameters, including physiological parameters.

2. Description of Related Art

The combination of biosensors and microelectronics has resulted in the availability of portable diagnostic medical equipment that has improved the quality of life for countless people. Many people suffering from disease or disability who, in the past, were forced to make routine visits to a hospital or doctor's office for diagnostic testing currently perform diagnostic testing on themselves in the comfort of their own homes using equipment with accuracy to rival laboratory equipment.

Nonetheless, challenges in the biosensing field have remained. For example, although many diabetics currently utilize diagnostic medical equipment in the comfort of their own homes, the vast majority of such devices still require diabetics to draw their own blood and inject their own insulin. Drawing blood typically requires pricking a finger. For someone who is diagnosed with diabetes at an early age, the number of self-induced finger pricks over the course of a lifetime could easily reach into the tens of thousands. In addition, the number of insulin injections may also reach into tens of thousands. Under any circumstances, drawing blood and injecting insulin thousands of times is overly invasive and inconvenient at best and most likely painful and emotionally debilitating.

Some medical conditions have been amenable to automated, implantable sensing. For example, thousands of people with heart conditions have had pacemakers or defibrillators implanted into their bodies that utilize sensors for monitoring the oxygen content of their blood. Ideally, these sensors should be able to determine whether, for example, a person's heart is running very efficiently at a high heart rate or whether a person's heart has entered defibrillation. In order to effectively make this determination, an accurate sensor must be employed. Unfortunately, oxygen sensors implanted into the body have, thus far, typically required frequent and periodic checking and recalibration. In fact, one of the "holy grails" of the pacemaker industry has been an accurate, no drift, no calibration oxygen sensor. Up until now, such a sensor has been unavailable.

An ideal solution to the diagnostic requirements of those with disease or disability, absent an outright cure, is a sensing apparatus that may be implanted into the body and that may remain in the body for extended periods of time without the need to reset or recalibrate the sensor. Regardless of the particular application for such a sensor system, in order to effect such a system, the associated sensor must remain accurate, exhibit low drift and require no recalibration for extended periods of time.

Thus, an ideal implantable sensing apparatus would provide for a sensing apparatus that may be inserted into a vein, artery or other part of a body while being unobtrusive, easy to insert and remove, yet accurate and reliable. Embodiments of the present invention provides such a system.

SUMMARY OF THE DISCLOSURE

Embodiments of the present invention relate to a sensing apparatus. A sensing apparatus includes a cable having a first end and a second end, a connector residing at the first end of the cable and a sensor module residing at the second end of the cable. The cable, the connector and the sensor module may be unidiametrical.

The cable may comprise a core, a conductive element wrapped around the core, and a first tubing covering the core and the conductive element. The core may be polyester. The conductive element may be a ribbon cable. The conductive element may include wires. The wires may be platinum. The wires may be welded to the connector and the sensor module. Alternatively, the wires may be crimped to the connector. The first tubing of the cable may be radio opaque. A second tubing may cover the first tubing. A window may be cut into the second tubing.

The sensor module may have a first end and a second end. Beads may encapsulate the first end and the second end. The sensor module may also have a spacing element. A height of the spacing element may be greater than a height of the beads.

The sensing apparatus may also include an enzyme. The enzyme may be glucose oxidase or human serum albumin. The enzyme may be a protein matrix. The enzyme may be hydrated.

A method of making a sensing apparatus may comprise obtaining a connector; obtaining a cable; obtaining a sensor module; attaching a first end of the cable to the connector; and attaching a second end of the cable to the sensor module. The method may further include forming beads over ends of the sensor module; inserting a spacing element between the beads; covering the sensor module with a tubing of the cable; cutting a window in the tubing of the cable; and inserting an enzyme in the sensor module.

These and other objects, features, and advantages of embodiments of the invention will be apparent to those skilled in the art from the following detailed description of embodiments of the invention when read with the drawings and appended claims.

BRIEF DESCRIPTION OF THE DRAWINGS

FIG. 3A is a perspective view of an electrode side of a generalized sensor module configuration with encapsulated ends according to an embodiment of the present invention.

FIG. 3B is a perspective view of an electronics side of a generalized sensor module configuration with encapsulated ends according to an embodiment of the present invention.

DETAILED DESCRIPTION

In the following description of preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the preferred embodiments of the present invention.

Embodiments of the present invention comprise a sensing apparatus including, without limitation, a sensor module, a sensor lead and a connector. As will be explained below in greater detail, the sensor module may comprise, without limitation, an enzyme and one or more spacers. The lead may comprise, without limitation, a core, a conductor, a first tubing and a second tubing. In embodiments of the sensing apparatus, each element of the sensing apparatus may be modified separately or in conjunction with another element according to the application or environment in which sensing apparatus is used. Thus, the sensing apparatus may be seen as a plurality of modular, individual elements, each of which may be modified and combined with one another to provide a sensing apparatus that may be used in a variety of applications, in a variety of environments, and implanted in a variety of locations.

Figure 1:
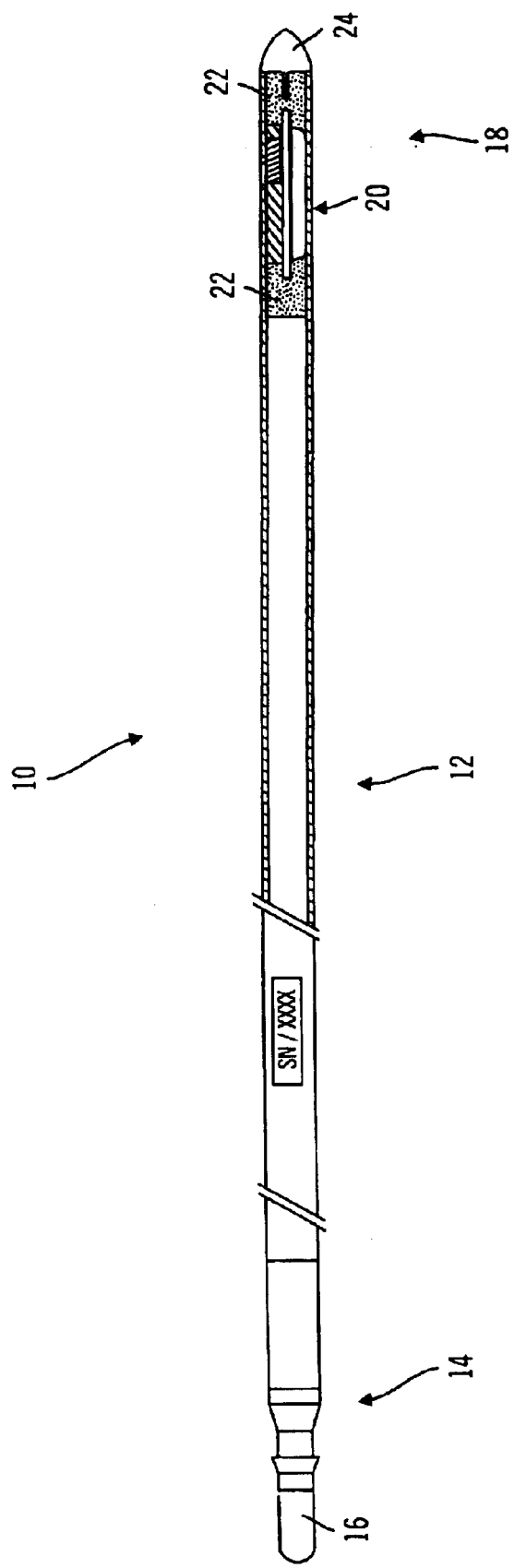
FIG. 1 is a perspective view of a generalized sensing apparatus configuration according to an embodiment of the present invention.

FIG. 1 shows a generalized sensing apparatus configuration according to an embodiment of the present invention. A sensing apparatus 10 includes a sensor lead 12, a first end 14 comprising a connector 16 and a second end 18 comprising a sensor module 20. Molded onto each end of the sensor module 20 are beads 22. An ogive, or bullet shaped, tip 24 attaches to a bead 22 that is opposite the sensor lead 12 such that the entire assembly is streamlined in a fluidic environment, such as a bloodstream. The sensor lead 12 comprises tubing that attaches to the ogive tip 24. The entire sensing apparatus 10 may be placed in a vein or other area within a human body using a process according to an embodiment of the present invention to be discussed below.

The connector 16 may be a male, female or other type connector. The connector 16 may provide for multiple conductive paths, thereby accommodating a variety of sensor lead 12 configurations. Also, the connector 16 may be made from a variety of materials. For example, the connector 16 may be made from any material that is electrically conductive yet chemically inert.

Figure 2B:
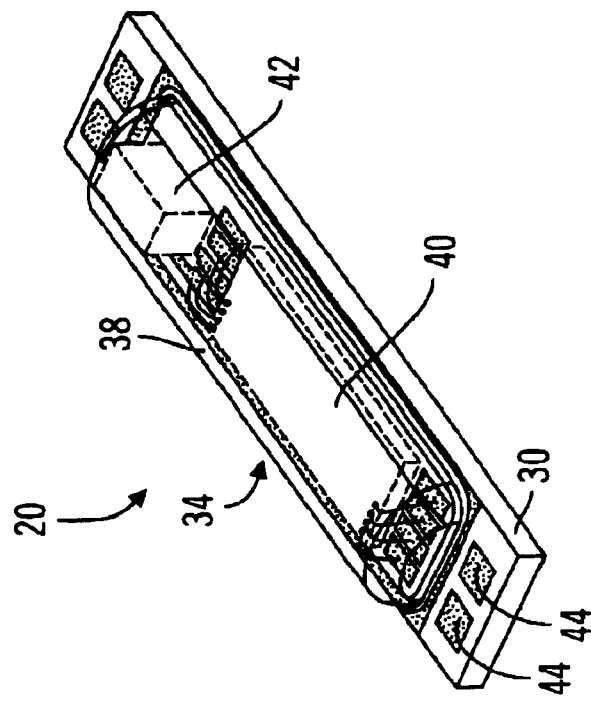
FIG. 2B is a perspective view of an electronics side of a generalized sensor module configuration according to an embodiment of the present invention.
Figure 2A:
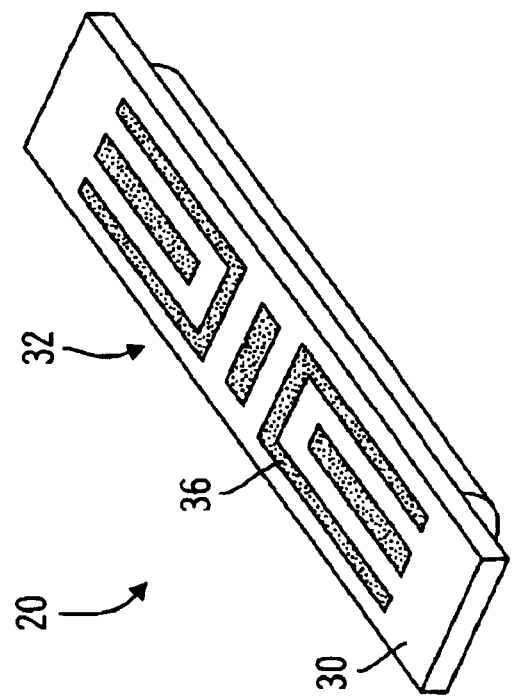
FIG. 2A is a perspective view of an electrode side of a generalized sensor module configuration according to an embodiment of the present invention.

FIGS. 2A and 2B show a generalized sensor configuration according to an embodiment of the present invention. A sensor module 20 may include a substrate 30 having a sensing element side 32 and an electronics side 34. The substrate 30 may be made from ceramic or other materials. As can be seen in FIG. 2A, electrodes 36 may be deposited onto the sensing element side 32 of the substrate 30. The electrodes 36 may interface with a sensing element (not shown) which will be described below. As can be seen in FIG. 2B, the electronics side 34 of the substrate 30 may include a lid 38 that covers a variety of electronics, such as, for example, an integrated circuit 40 and a capacitor 42. The electronics side 34 of the substrate 30 may also include welding pads 44 to which wire leads may be welded as well as other types of pads and traces common to electronic circuitry. The electrodes 36 and the electronics on the electronics side 34 of the substrate 30 provide the basis for electrochemical measurement. According to one embodiment of the invention, the sensor module 20 may be utilized for oxygen sensing. However, the sensor module is not limited to this application and may also be utilized in other applications such as, for example, for ion, neurotransmitter or nitric oxide sensing.

FIGS. 3A and 3B show further details of a generalized sensor configuration according to an embodiment of the present invention. In FIG. 3A, a portion of the electrode pattern may be encapsulated by the beads 22. In FIG. 3B, beads 22 may be molded over the ends of the substrate 30 such that the welding pads 44 and any wires welded to the welding pads 44 are encapsulated within the beads 22. In addition, the beads 22 may also encapsulate a core of the sensor lead 12, thereby giving the core an anchor. The beads 22 may be formed over the ends of the substrate 30 using a mold. The substrate 30 may be placed into the mold and the ends of the substrate 30 subsequently covered with an epoxy or other encapsulating material.

Figure 4:
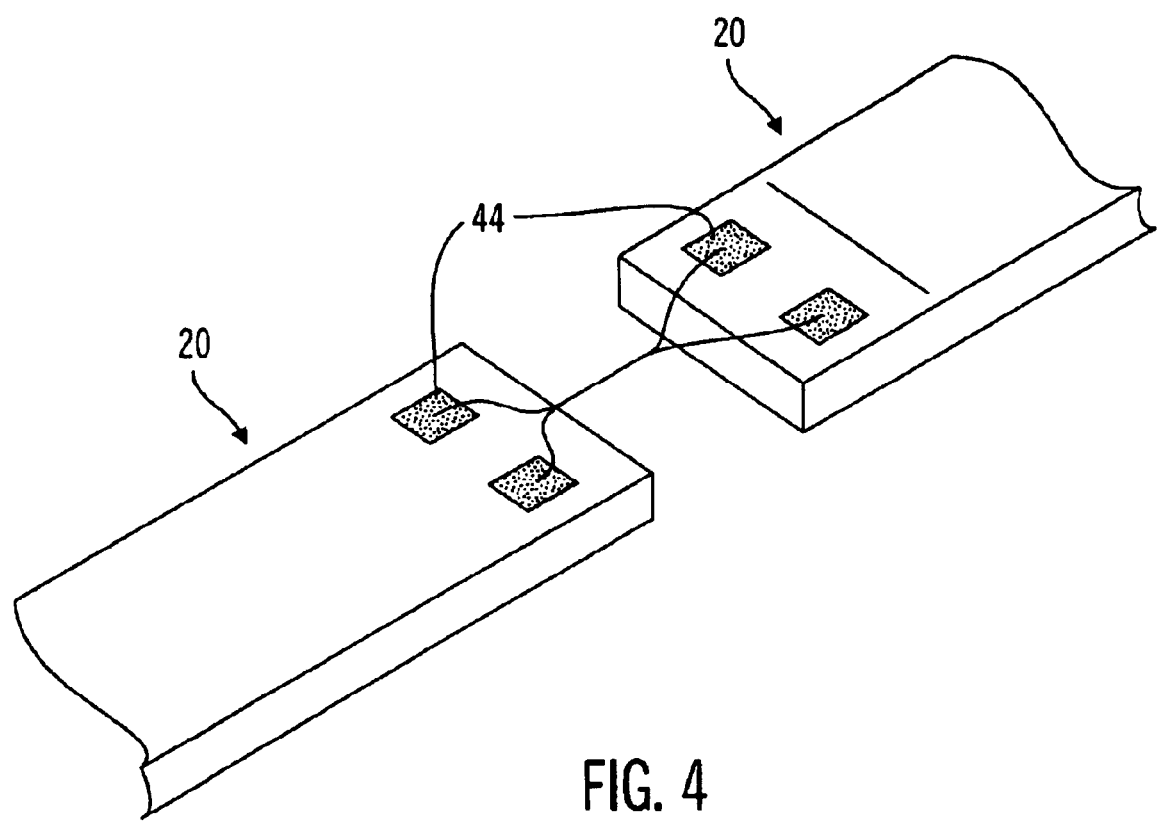
FIG. 4 is a perspective view of a sensor module configuration wherein two sensor modules are connected together in a "daisy-chain" fashion according to an embodiment of the present invention.

FIG. 4 shows a sensor configuration wherein two sensor modules 20 are connected together in a "daisy-chain" fashion. In this configuration, the welding pads 44 may be straight-through pads, such that electrical continuity exists between corresponding welding pads 44 on opposite sides of each sensor module 20. Thus, by serially connecting a welding pad 44 of one sensor module 20 to a corresponding welding pad 44 of another sensing module 20, the sensing modules 20 may be individually addressed using a two-wire line and unique addresses.

Figure 5:
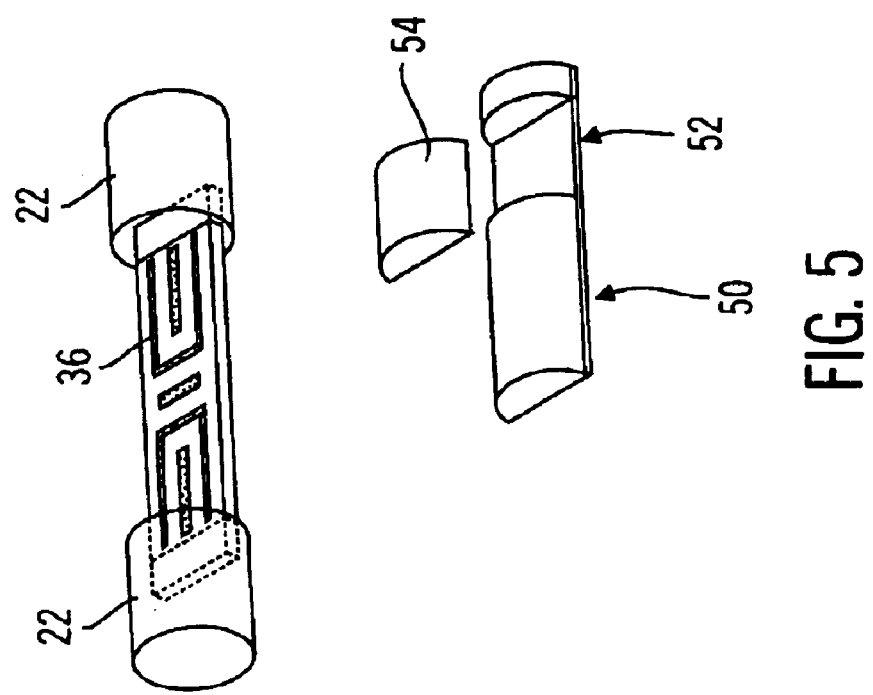
FIG. 5 is a perspective view of a sensor module with spacers according to an embodiment of the present invention.

FIG. 5 shows a sensor module with spacers according to an embodiment of the present invention. A first spacing element 50 may be placed over the electrodes 36, fitting into a recess between the beads 22. The first spacing element 50 may be thought of as a spacer shim because it has the function of maintaining a certain distance or space between the electrodes 36 and an enzyme which may eventually be placed within the sensor module 20. The floor 52 of the first spacing element 50 may be such that it allows the passage of oxygen. If, for example, the first spacing element is made from silicone or polydimethylsiloxane, the floor 52 of the first spacing element 50 will pass oxygen but will not pass other compounds found in the bloodstream, such as glucose.

An enzyme and space may be used to fine tune sensor performance. The size and configuration of the enzyme and spacer may be modified to effect of variety of sensing characteristics For example, the enzyme and spacer size and configuration may be modified to improve dynamic range, reduce noise due to oxygen transients, and increase sensing apparatus lifetime. The configuration of the enzyme and spacer may be driven by a variety of factors including, without limitation, the need to measure a physiological parameter, such as, for example, blood glucose, and the need to keep membranes of the sensor module 20 in compression during the lifetime of the device.

A second spacing element 54 fits within the first spacing element 50 and provides support for a window that may be cut into tubing that covers the sensor module 20 and attaches to the ogive tip 24. After the window has been cut, as will be explained below, the second spacing element 54 may be discarded and an enzyme or other sensing catalyst may be disposed in its place.

An outer tubing of the sensor lead 12 may be pulled over the first spacing element 50. The outer diameter of the first spacing element 50 may be such that it is greater than the inner diameter of the outer tubing of the sensor lead 12. Thus, when the outer tubing of the sensor lead 12 is pulled over the first spacing element 50 the first spacing element 50 may be forced against the electrodes 36 on the substrate 30 by the contraction force of the outer tubing.

The spacing elements may be made from the same mold used to form the beads 22. If the same mold that was used to form the beads 22 is used to form the spacing elements 50, 54, the spacing elements 50, 54 will form a precise fit with the beads 22. The spacing elements 50, 54 may be made from silicon or other suitable material.

In addition, the height of the first spacing element 50 may extend beyond the height of the beads 22. When the height of the first spacing element 50 and the beads 22 are offset, any compression upon the first spacing element 50, such as that that might be applied when the outer tubing of the sensor lead 12 is slipped over the sensor module 20, tends to stabilize the dimensions of the elements of the apparatus, such as membranes that may exist above the electrodes 36, that may change through chemical reaction.

Figure 6A:
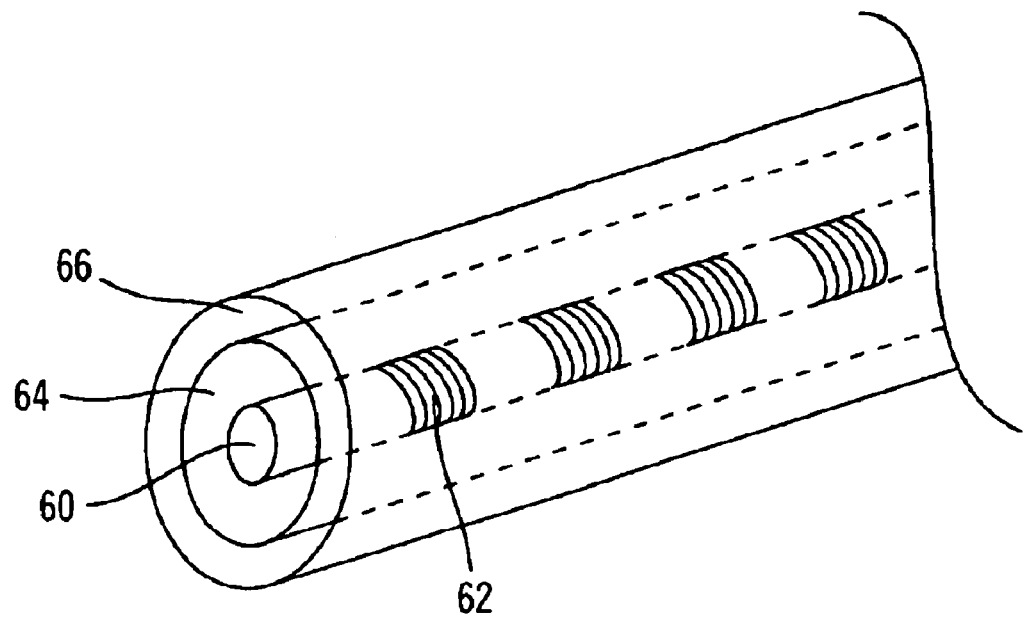
FIG. 6A is a perspective view of a generalized sensor lead according to an embodiment of the present invention.

FIG. 6A shows a generalized sensor lead 12 according to an embodiment of the present invention. At the center of the sensor lead 12 may be a core 60. The core 60 may be a material such as, for example, polyester or other material, or a commercially available material such as, for example, DACRON® or KEVLAR® (trademarks of du Pont de Nemours and Company), that provides shock absorption and strength to the sensor lead 12. According to one embodiment of the present invention, a polyester core may provide as much as 18–20 lbs. of tensile strength to the sensor lead 20. In addition, the core 60 limits sensor lead 12 elongation. Thus, if the sensing apparatus 10 has been implanted into a vein in a human body, a doctor or other medical professional who needs to remove the sensing apparatus 10 from the vein may pull on the sensor lead 12 without fear of excessively stretching it or breaking it. Various factors may influence the size of the core 60 and the material used for the core 60 such as, for example, the overall diameter, device stiffness, and sensor lead 12 attachment scheme.

Wrapped around the core 60 in a helical fashion is a conductive element 62. The conductive element 62 may be a flat cable or ribbon cable having multiple conductor wires. The conductive element 62 may also be a laminate structure conducive to being wrapped around the core 60 with a pitch in between the windings such that the conductive element 62 has enough flexibility to move with the core 60 if the core 60 is stretched. The helical nature of the winding also contributes to the flexibility of the conductive element 62 if the core 60 is stretched or otherwise moved. The conductive element 62 may include only a few wires, such as for example, three wires or four wires. Alternatively, if the application requires a large number of data channels or high current carrying capacitor, the conductive element 62 may include a larger number of wires, such as, for example, five wires, ten wires or more. The size of the conductive element 62, the number of wires in the conductive element 62, and the materials used as the conductive element 62 may be influenced by a variety of factors including, without limitation, sensing apparatus application and signal transmission requirements. For example, the size of the conductive element 62, the number of wires in the conductive element 62, and the materials used as the conductive element 62 may be chosen depending on whether the sensing apparatus is used in digital or analog applications or depending on a particular communications protocol. The strength of the conductive element 62 needed for a particular application may be a factor in determining wire size. In addition, the wires used in the conductive element 62 may be, for example, platinum, iridium, MP35, gold or silver, or other conductive material.

A first tubing 64 may be slid around the core 60 wrapped with the conductive element 60. The first tubing 64 may be made from a radio opaque material such as silicone or may be made from other materials such as, for example, radio opaque polyurethane. The size and dimensions of the first tubing 64 and the materials used for the first tubing 64 may be influenced by a variety of factors including, without limitation, the overall stiffness requirements of the sensor lead 12 according to the application of the sensing apparatus 10.

A second tubing 66 may be slid around the first tubing 64. The second tubing 66 may be made from silicone or other material. The second tubing 66 may be used to provide oxygen transport and mechanical compression. Depending on the application, the surface of the second tubing 66 may be treated for biocompatibility, lubricity and stiffness.

Figure 6B:
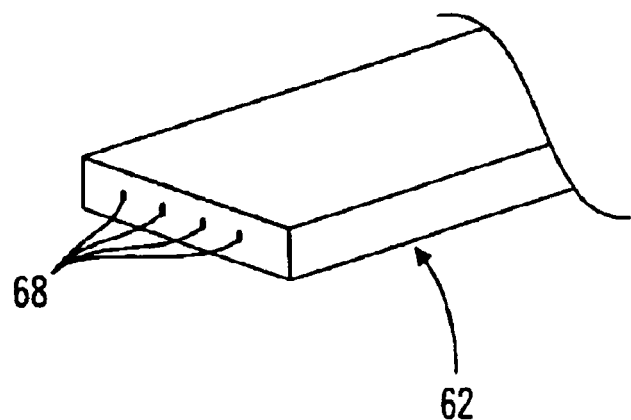
FIG. 6B is a perspective view of a conductor element according to an embodiment of the present invention.

According to an embodiment of the present invention the conductive element 62 may be a flat cable having four wires 68 as shown in FIG. 6B. The wires 68 may be platinum or another type of conductor, such as, for example, a noble metal. The diameter of each wire 68 may be as thin as one one-thousandth of an inch or thinner and the entire cable may be molded with TEFLON or another insulator such that the wires are insulated from one another. Because much of the strength of the sensor lead 12 may be derived from the core 60, the wires themselves need not be chosen for strength. Thus, the wires need a diameter only as large as necessary to carry the currents being generated by the devices to which the sensor lead 12 is attached. For example, in the case where the sensor module 20 employs an electrochemical sensing element, the currents generated may be on the order of hundreds of nanoamps or tens of microamps. The type of wire used in the sensor lead 12 may be chosen accordingly. In the case where the sensor lead 12 is attached to a pacemaker, the wires may be chosen such that they can accommodate a current of a few milliamps, a typical value for heart stimulating pulses used in pacemakers. Thus, in the case where the sensor lead 12 is inserted into a vein, a metal such as platinum may be used as the wire. Platinum, although very fragile at the small diameters required for carrying the electrical currents just mentioned, such as, for example, one one-thousandth of an inch, is chemically inert and corrosion resistant and, thus, desirable in a fluidic environment, such as blood. However, because the wires are so thin, they may be generally less intrusive to the environment in which they are placed than larger diameter wires typically used in an in-vivo application. Thus, according to embodiments of the present invention, a thin, fragile wire may be used where, traditionally, larger diameter, strong wires have been used. Thus, a wire made from a metal such as platinum may be employed.

In order to connect the wires to the relevant portions of the connector 16 and the sensor module 20 the cable may be stripped and the wires connected together in groups of two. Once connected together, the wires may be viewed as two wires having two strands each. Thus, the wires are redundant and should one break, another is available to maintain electrical continuity. One of the wire pairs may then be crimped and welded to the connector 16 and the other wire pair may be spot welded to the wire pads 44 on the sensor module 20.

A completed sensor lead 12 may be labeled for identification or other purposes. A variety of labeling materials may be used for labeling. According to one embodiment of the present invention, any labeling material may be used so long as the material chosen remains visible after sterilization of the sensing apparatus 10.

Also, the label may be placed in a variety of positions on the sensor lead 12. For example, according to one embodiment of the present invention, the label may be placed on the outer surface of the first tubing 64 in between the first tubing 64 and the second tubing 66 using an green-colored, epoxy based ink that is biocompatible and that does not leach toxic materials into or out of the sensor lead 12.

Figure 7:
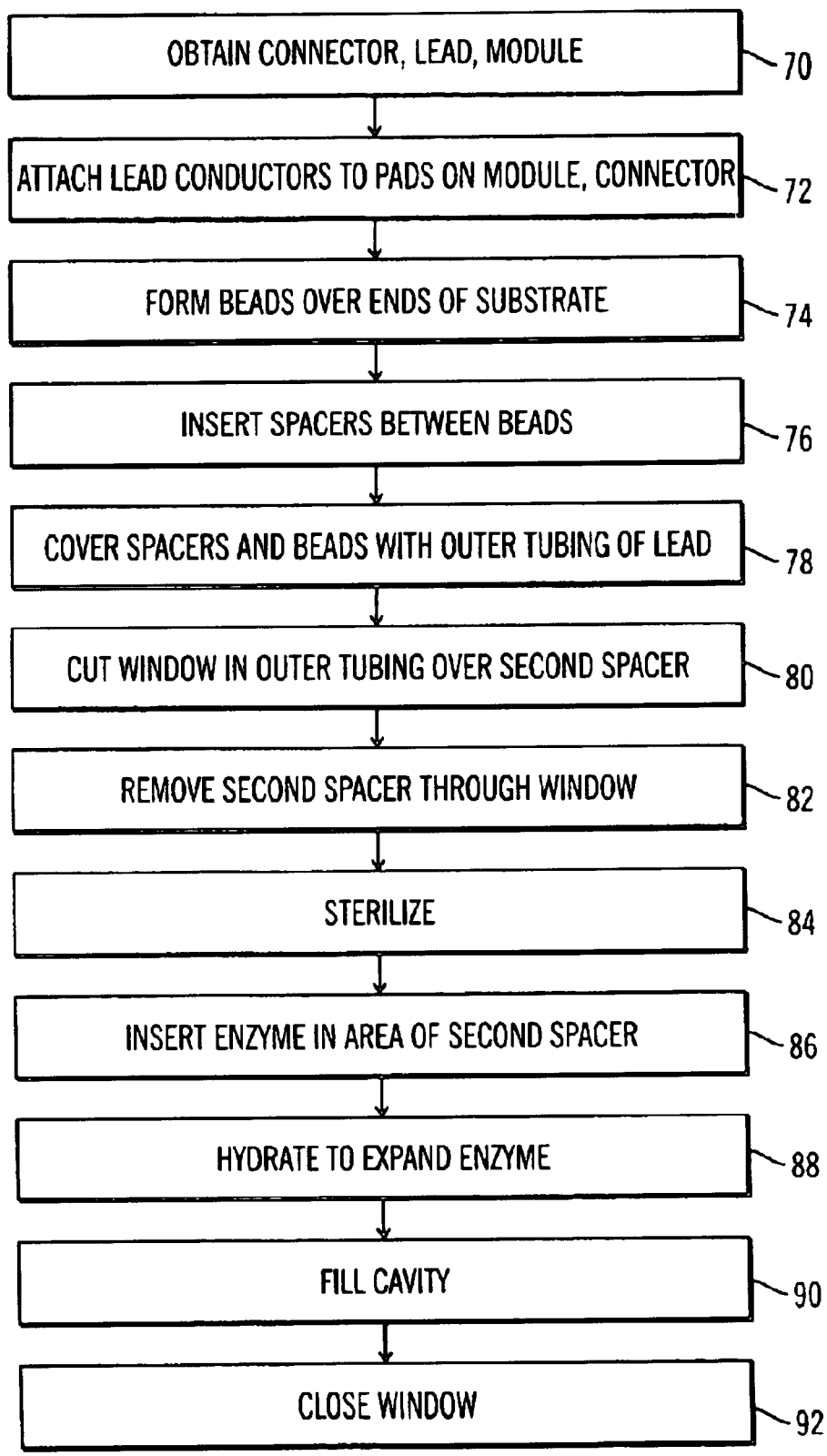
FIG. 7 is a process for making a sensing apparatus according to an embodiment of the present invention.

FIG. 7 shows a process for making a sensing apparatus according to an embodiment of the present invention. At step 70, the connector 16, the sensor lead 12 and the sensor module 20 are obtained. At step 72 the wires in the conductive element of the sensor lead 12 are attached to the pads 44 on the substrate 30 of the sensor module 20 and to the connector 16 The wires in the conductive element may be welded or otherwise attached to the pads 44 and crimped or otherwise attached to the connector.

At step 74, beads 22 are formed over the ends of the substrate 30 such that the welding pads, a portion of the electrodes 36 and the core 60 are encapsulated within the beads 22. In addition, an ogive tip 24 may be glued or otherwise attached to a bead 22 opposite the sensor lead 12.

At step 76 spacing elements may be inserted in between the beads 22. The spacers may comprise a first spacing element 50 and a second spacing element 54 At step 78, an outer tubing of the sensor lead 12 may be pulled over the sensor module 20 and attached to the ogive tip 24 attached to the bead 22 opposite the sensor lead 12.

Figure 8:
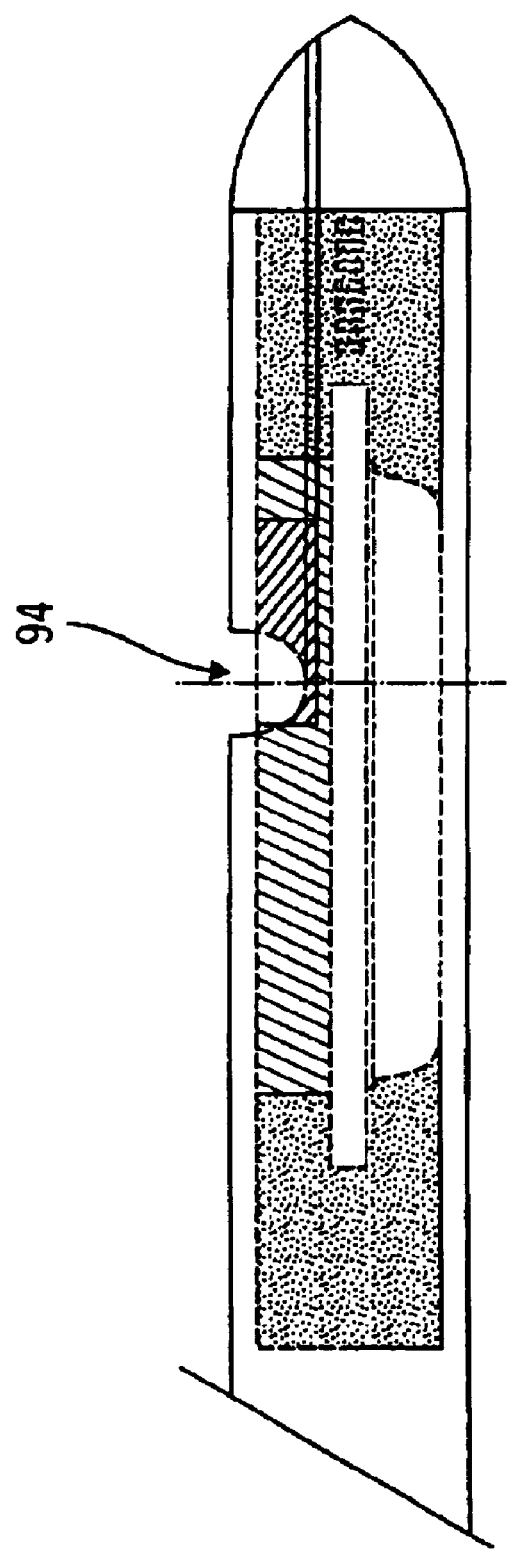
FIG. 8 is a side showing a window cut into an outer tubing of the sensor lead according to an embodiment of the present invention.

At step 80, a window may be cut in the outer tubing of the sensor lead 12 over the second spacing element 54. The window may be cut and placed in a manner suitable for the application of the sensing apparatus 10 and such that the sensitivity of the apparatus is advantageous. For example, if the sensing apparatus is to be used in a glucose monitoring application, such as might be used in the case of a diabetic, the window may be cut with a particular width and at such a place on the outer tubing of the sensor lead 12 such that oxygen influx into the enzyme is aided. In glucose sensing applications, a typical window width may be five thousandths of an inch, or may be ten to twenty thousandths of an inch. In addition, window depth may be anywhere from about four thousandths of an inch to ten thousandths of an inch. The response time of the device may also be adjusted by the cut and placement of the window. A window 94 cut into an outer tubing of the sensor lead 12 may be seen in FIG. 8.

The second spacing element 54 may be removed at step 82 and the entire sensing apparatus 10 may be sterilized. The sterilization step 84 may be implemented using a variety of sterilization techniques. For example, the entire sensing apparatus 10 (which may or may not include an enzyme, protein, or other physiological parameter sensor) may be put into an ethylene oxide (ETO) gas such that the ETO gas permeates all of the elements of the sensing apparatus 10. After sterilization, the sensing apparatus may be stored until it is ready for use.

If desired, an enzyme may be put in the place of the second spacing element 54 through the window at step 86. The enzyme may be any of a variety of enzymes that may be employed for sensing. For example, if physiological parameter sensing is desired, one or more proteins may be used as the enzyme. According to one embodiment of the present invention, a combination of glucose oxidase and human serum albumin may be used concurrently in a solid matrix form to form a sensor matrix protein (SMP). The SMP may be cross-linked together or glymerized using glutaraldehyde or other suitable chemical such that a three-dimensional structure is created.

The enzyme may be hydrated at step 88 such that it expands to form a tight fit and to fill the area left by the removal of the second spacing element 54. The enzyme may initially be in a slightly desiccated state when placed into the area vacated by the second spacing element 54. Although such a desiccated state facilitates placement, space may exist between the enzyme and the surround area of the sensor module 20. Thus, the surrounding area and the enzyme may be hydrated with a sterile buffer, thereby swelling the enzyme and forming a compression fit with the first spacing element 50. Any cavity left in surrounding area after the enzyme has been hydrated may be filled at step 90 with, for example, a hydrogel, such as, for example, methacrylate or other hydrophilic acrylic, that is permeable to the steriliant. Subsequently, the hydrogel may be polymerized using a UV polymerization process.

At step 92, the window may be closed and the sensing apparatus 10 may be sterilized again in a manner that is not damaging to the enzyme. For example, a more dilute form of the glutaraldehyde may be used to sterilize the sensing apparatus 10 after the enzyme has been place in the first spacing element 50. The sensing apparatus 10 may then be used as necessary.

Figure 9:
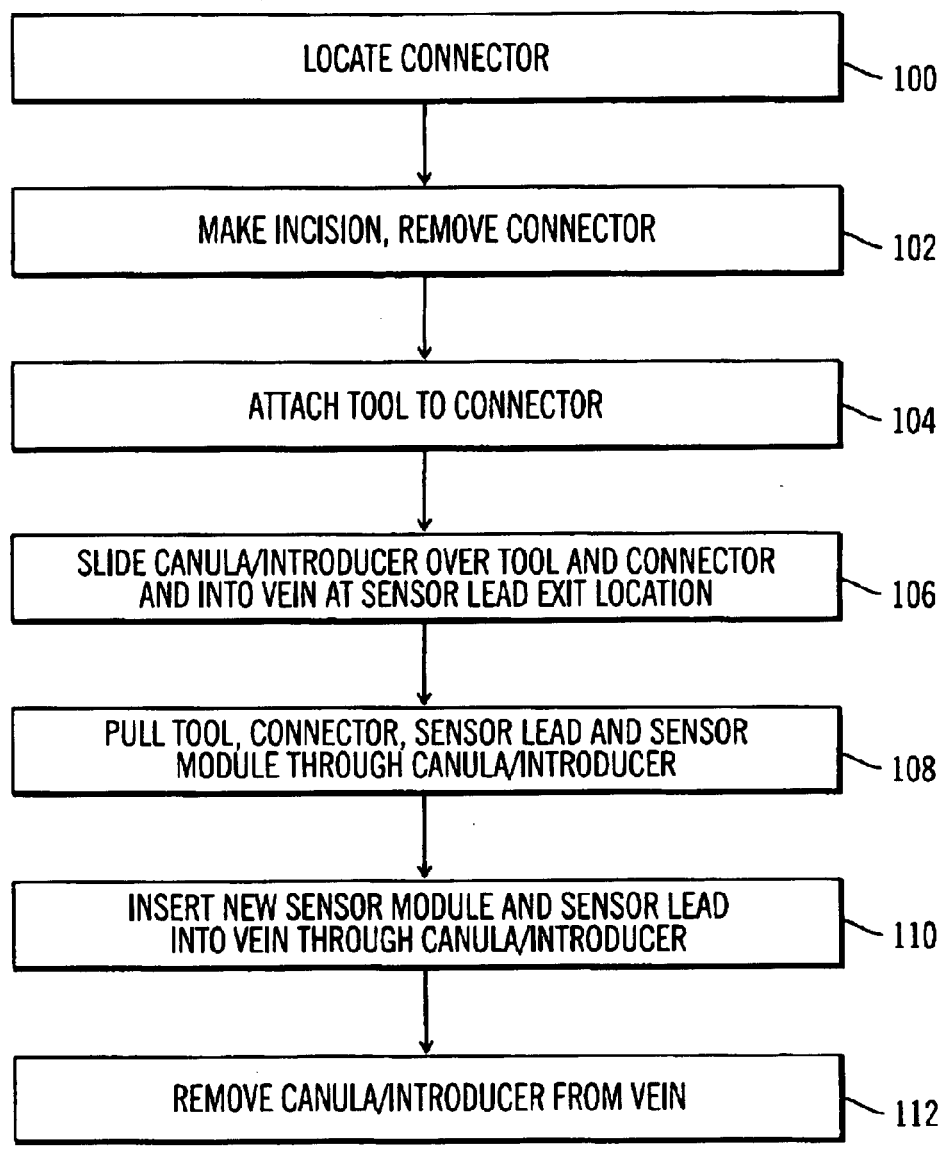
FIG. 9 is a process for removing or replacing a sensing apparatus according to an embodiment of the present invention.

FIG. 9 shows a process for removing or replacing a sensing apparatus from a vein or artery. The vein or artery may belong to a human being or other animal. At step 100, a connector 16 that has been implanted into a vein along with the rest of the sensing apparatus is found by locating it under the skin by touch and feel in the general area that the connector 16 should be residing. At step 102, an incision is made into the skin and the connector 16 may be brought out of the skin.

At step 104, a tool with clamping fingers is placed over the connector 16 such that the fingers close onto the connector 16 and form a secure connection with the connector 16. A canula/introducer is then slid over the tool and the connector at step 106 into the vein at the location of the incision. Fabricating the connector 16, the sensor lead 12, and the sensor module 20 to be unidiametrical facilitates sliding the canula/introducer over them. While the canula/introducer remains in the vein, the tool, connector 16, sensor lead 12 and sensor module 20 may be pulled through the canula/introducer at step 108, thereby removing the sensing apparatus 10 from the vein.

At step 110, a new sensing apparatus may be inserted into the vein. Once the new sensing apparatus is inserted into the vein, the canula/introducer may be removed at step 112 and the incision may be sewn up.

While particular embodiments of the present invention have been shown and described, it will be obvious to those skilled in the art that the invention is not limited to the particular embodiments shown and described and that changes and modifications may be made without departing from the spirit and scope of the appended claims.

What is claimed is:

1. A sensing apparatus comprising:
    a cable having a first end, a second end and a core, wherein the core extends from the first end of the cable to the second end of the cable;
    a connector residing at the first end of the cable; and
    a sensor module residing at the second end of the cable; and
    a conductive element extending from the connector to the sensor module, the conductive element being helically wrapped around at least a substantial length of the core;
    wherein the sensor module comprises a first end and a second end; and
    wherein beads encapsulate the first end and the second end.

2. A sensing apparatus according to claim 1, wherein the sensor module further comprises a spacing element.

3. A sensing apparatus according to claim 2, wherein a height of the spacing element is greater than a height of the beads.

4. A sensing apparatus according to claim 2, wherein the spacing element resides between the beads.

5. A sensing apparatus according to claim 1, wherein the sensor module further comprises a spacing element, wherein the spacing element resides between the beads.

6. A method of making a sensing apparatus comprising:
    obtaining a connector;
    obtaining a cable;
    obtaining a sensor module;
    attaching a first end of the cable to the connector;
    attaching a second end of the cable to the sensor module;
    forming beads over ends of the sensor module;
    inserting a spacing element between the beads;
    covering the sensor module with a tubing of the cable;
    cutting a window in the tubing of the cable; and
    inserting an enzyme in the sensor module.

7. A method according to claim 6, wherein the enzyme is hydrated.

8. A sensing apparatus comprising:
    a cable having a first end, a second end and a core, wherein the core extends from the first end of the cable to the second end of the cable;
    a connector residing at the first end of the cable;
    a sensor module residing at the second end of the cable; and
    a conductive element extending from the connector to the sensor module, the conductive element being helically wrapped around at least a substantial length of the core;
    wherein the sensor module further comprises a spacing element, and
    wherein the spacing element comprises a first spacing element and a second spacing element, the first spacing element being configured to couple with the second spacing element, wherein the second spacing element is removable to leave a space in the first spacing element for receiving a sensing catalyst.

9. A sensing apparatus according to claim 8, wherein the first spacing element comprises a floor, the floor of the first spacing element being configured to allow the passage of oxygen.

10. A sensing apparatus comprising:
    a cable having a first end, a second end and a core, wherein the core extends from the first end of the cable to the second end of the cable;
    a connector residing at the first end of the cable;
    a sensor module residing at the second end of the cable; and
    a conductive element extending from the connector to the sensor module, the conductive element being helically wrapped around at least a substantial length of the core;
    wherein the sensor module further comprises a first spacing element and a second spacing element, the first spacing element being configured to couple with the second spacing element;
    wherein the first spacing element comprises a floor, the floor of the first spacing element being configured to allow the passage of oxygen; and
    wherein the second spacing element is removable to leave a space in the first spacing element for receiving a sensing catalyst.

* * * * *